(12) United States Patent  
Goldfain et al.

(10) Patent No.: US 9,345,407 B2
(45) Date of Patent: *May 24, 2016

(54) METHOD AND APPARATUS FOR ANALYZING SUBSURFACES OF A TARGET MATERIAL

(71) Applicant: Welch Allyn, Inc., Skaneateles Falls, NY (US)

(72) Inventors: Ervin Goldfain, Syracuse, NY (US); Raymond A. Lia, Auburn, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/643,187

(22) Filed: Mar. 10, 2015

(65) Prior Publication Data

US 2015/0173620 A1    Jun. 25, 2015

Related U.S. Application Data

(63) Continuation of application No. 13/971,950, filed on Aug. 21, 2013, now Pat. No. 9,014,792, which is a continuation of application No. 13/293,337, filed on Nov. 10, 2011, now Pat. No. 8,543,192.

(51) Int. Cl.
*A61B 5/00* (2006.01)
*G01B 9/02* (2006.01)

(52) U.S. Cl.
CPC .............. *A61B 5/0066* (2013.01); *A61B 5/0073* (2013.01); *A61B 5/0075* (2013.01); *A61B 5/0084* (2013.01); *G01B 9/02091* (2013.01); *Y10T 29/49002* (2015.01)

(58) Field of Classification Search
CPC .. A61B 5/0066; A61B 5/0073; A61B 5/0075; A61B 5/0084; G01B 9/02091; Y01T 29/49002
See application file for complete search history.

(56) References Cited

U.S. PATENT DOCUMENTS

| | | | |
|---|---|---|---|
| 3,698,387 A | 10/1972 | Moore | |
| 6,334,067 B1 | 12/2001 | Brabrand | |
| 7,101,365 B1 | 9/2006 | Sharon | |
| 7,399,275 B2 | 7/2008 | Goldfain | |
| 8,543,192 B2 | 9/2013 | Goldfain et al. | |
| 9,014,792 B2 * | 4/2015 | Goldfain | A61B 5/0066 356/477 |
| 2008/0062429 A1 | 3/2008 | Liang | |
| 2009/0185191 A1 | 7/2009 | Boppart | |

(Continued)

OTHER PUBLICATIONS

PCT International Search Report and Written Opinion, PCT/US2012/060409, Dec. 28, 2012, 9 pages.

(Continued)

*Primary Examiner* — Michael Rozanski
(74) *Attorney, Agent, or Firm* — Guntin & Gust, PLC; Robert Gingher

(57) ABSTRACT

A system that incorporates teachings of the present disclosure may include, for example, a method for aligning first and second light signals on an optical path directed to a target, where the first light signal provides a visualization of the target, and a portion of the second light signal reflects from at least one subsurface of the target. The method also includes aligning a first focal point of the first light signal and a second focal point of the second light signal, where the first focal point is at least in a first proximate location of the second focal point, and adjusting a first position of the first and second focal points to be in at least a second proximate location of the target without adjusting the at least first proximate location of the first focal point relative to the second focal point. Other embodiments are disclosed.

20 Claims, 9 Drawing Sheets

(56) References Cited

U.S. PATENT DOCUMENTS

2010/0177185 A1    7/2010    Woerlein
2011/0130652 A1    6/2011    Boppart

OTHER PUBLICATIONS

"Optical coherence tomography", http://en.wikipedia.org/wiki/Optical_coherence_tomography, Accessed Sep. 10, 2011.

Jung, et al., "Handheld Optical Coherence Tomography Scanner for Primary Care Diagnostics", TBME-00701-2010, pp. 1-4.

Nguyen, "Non-Invasive Assessment of Biofilm Growth in the Middle Ear Using a Portable Low-Coherence Interferometry System", University of Illinois at Urbana-Champaign, 2010.

Nguyen, et al., "Non-Invasive Optical Interferometry for the Assessment of Biofilm Growth in the Middle Ear", 2010 Optical Society of America, vol. 1, No. 4 / Biomedical Optics Express, pp. 1104-1116.

* cited by examiner

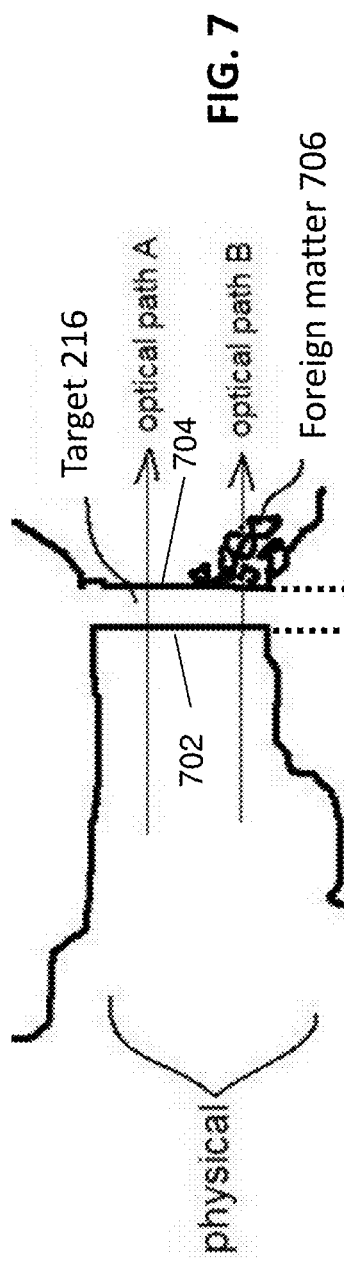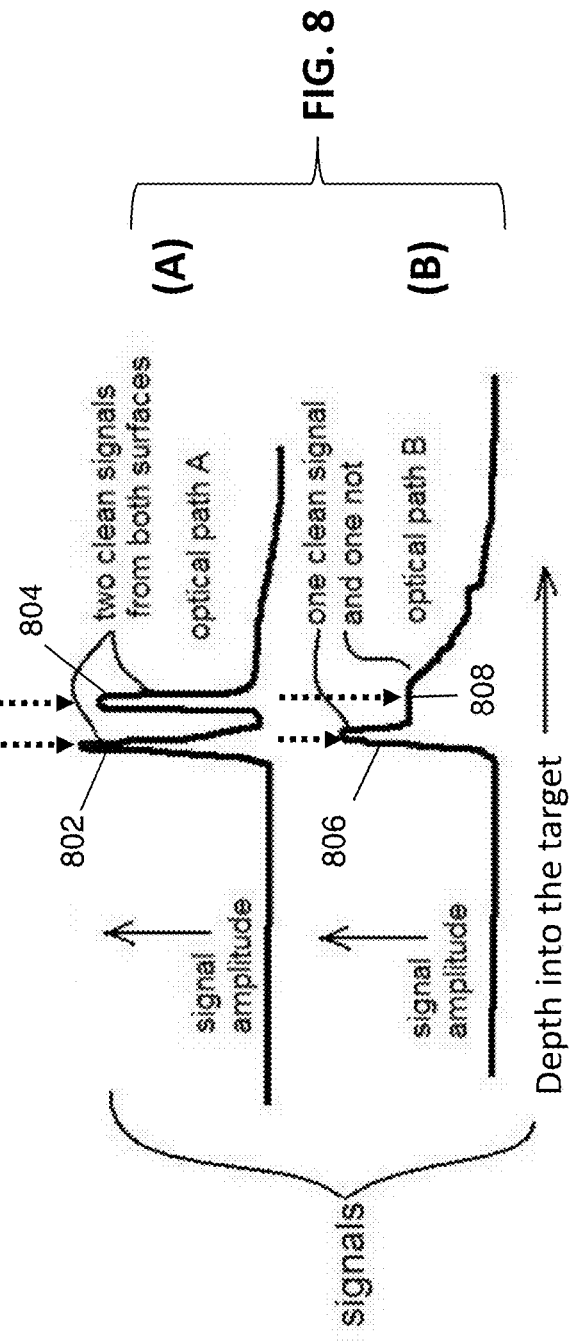

METHOD AND APPARATUS FOR ANALYZING SUBSURFACES OF A TARGET MATERIAL

CROSS-REFERENCE TO RELATED APPLICATIONS

This application is a continuation of and claims priority to U.S. patent application Ser. No. 13/971,950, filed Aug. 21, 2013, now U.S. Pat. No. 9,014,792, which is a continuation of U.S. patent application Ser. No. 13/293,337, filed Nov. 10, 2011, now U.S. Pat. No. 8,543,192. All sections of the aforementioned application(s) are incorporated herein by reference in its entirety.

FIELD OF THE DISCLOSURE

The present disclosure relates generally to a method and apparatus for analyzing subsurfaces of a target material.

BACKGROUND

Optical signal acquisition and processing methods such as optical coherence tomography (OCT) can be useful in medical as well as industrial applications. OCT, for example, can employ near infrared light to penetrate a range of subsurfaces of a target material. The scattered infrared light reflected from the target material can be used to generate micrometer resolution of three or two-dimensional images that are descriptive of the subsurfaces of the target material. In medical applications, these images can assist a physician to diagnose abnormalities in biological tissue. In industrial applications, images generated from materials that can absorb and reflect light signals such as near infrared light can provide engineers or other specialists insight into the subsurfaces of non-biological materials.

BRIEF DESCRIPTION OF THE DRAWINGS

Reference will now be made to the accompanying drawings, which are not necessarily drawn to scale.

FIGS. 7-9 depict illustrative embodiments of images produced by the imaging system of FIG. 5.

DETAILED DESCRIPTION

Figure 1:
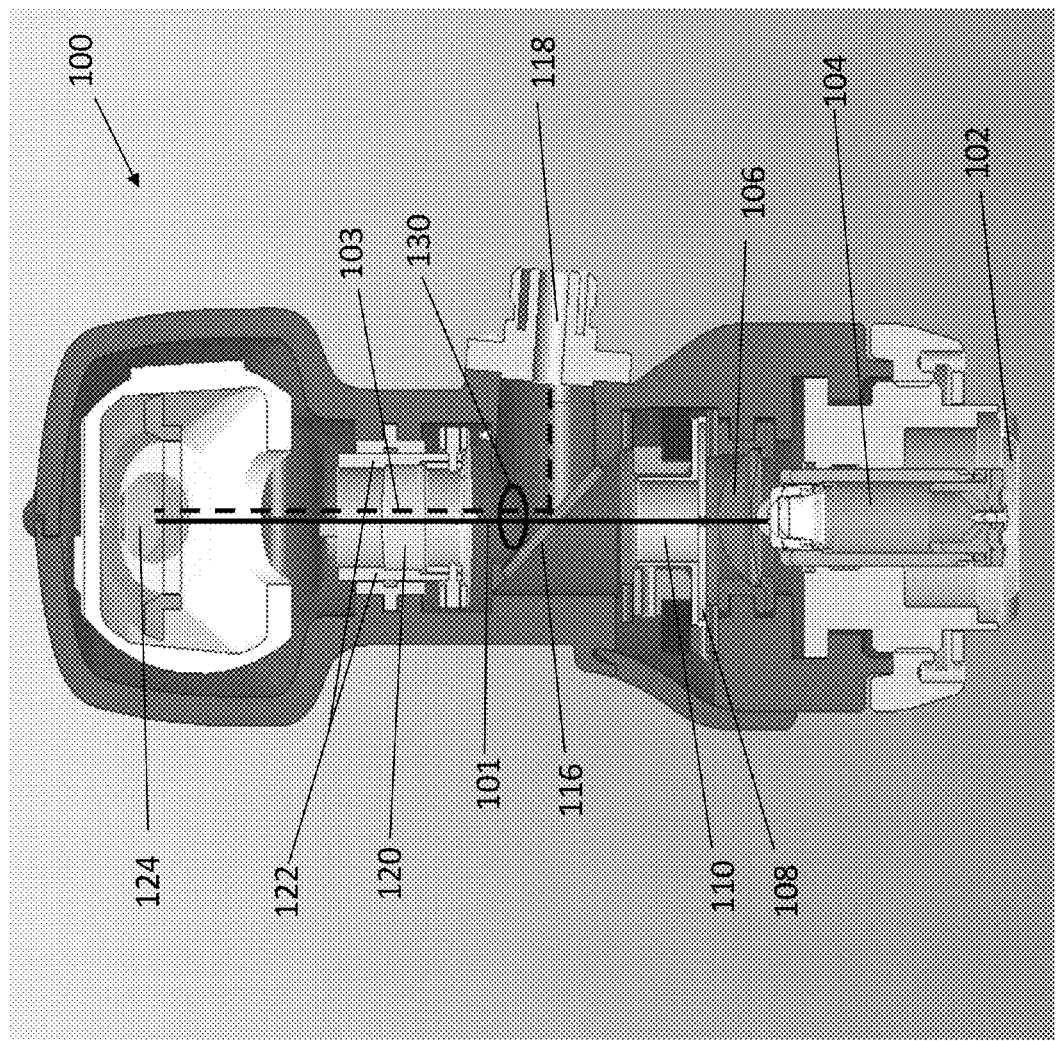
FIGS. 1-2 depict illustrative embodiments of rear and side cross-sectional views of a probe.

One embodiment of the present disclosure includes a medical device comprising a first light source for emitting a first light signal operating in a first region of the light spectrum that enables visualization of a target tissue, and a second light source for emitting a second light signal operating in a second region of the light spectrum that enables a reflection of a portion of the second light signal from at least one subsurface of the target tissue. The medical imaging device can further have a first optical device providing a coaxial optical path of the first light signal and the second light signal and providing a first focal point of the first light signal to be in at least a proximate location of a second focal point of the second light signal, and a second optical device to adjust the first focal point of the first light signal without changing the at least proximate location of the first focal point relative to the second focal point.

One embodiment of the present disclosure includes a method for aligning first and second light signals on an optical path directed to a target, wherein the first light signal provides a visualization of the target, and wherein a portion of the second light signal reflects from at least one subsurface of the target, aligning a first focal point of the first light signal and a second focal point of the second light signal, where the first focal point is at least in a first proximate location of the second focal point, and adjusting a first position of the first and second focal points to be in at least a second proximate location of the target without adjusting the at least first proximate location of the first focal point relative to the second focal point.

One embodiment of the present disclosure includes a computer-readable storage medium comprising computer instructions, which when executed by at least one processor, causes the at least one processor to receive from a probe a reflection of a portion of a second light signal from at least one subsurface of a target, and determine from the reflection an image descriptive of the at least one subsurface. The probe can be adapted to project an identifying mark on a surface of the target with a first light signal while at the same time applying the second light signal to the target, where the identifying mark is coincident with a first focal point of the first light signal, and where a second focal point of the second light signal is in a proximate location of the first focal point.

One embodiment of the present disclosure includes a computer-readable storage medium having computer instructions, which when executed by at least one processor, causes the at least one processor to receive from a probe a reflection of a portion of a second light signal from at least one subsurface of a target, and determine from the reflection an image descriptive of the at least one subsurface. In this embodiment the probe can be adapted to project an identifying mark on a surface of the target with a first light signal while at the same time applying the second light signal to the target, where the identifying mark is coincident with a first focal point of the first light signal, and where a second focal point of the second light signal is in a proximate location of the first focal point.

In an embodiment where the target is a non-biological composition, the computer-readable storage medium can have computer instructions to cause the at least one processor to detect from the image a fault in the non-biological composition.

In an embodiment where the target is a biological tissue, the computer-readable storage medium can have computer instructions to cause the at least one processor to detect from the image a presence of a biofilm or other form of biological abnormality.

In one embodiment the computer-readable storage medium can have computer instructions to cause the at least one processor to receive a reflection of the identifying mark at a camera sensing device, and project the identifying mark on a display.

Figure 2:
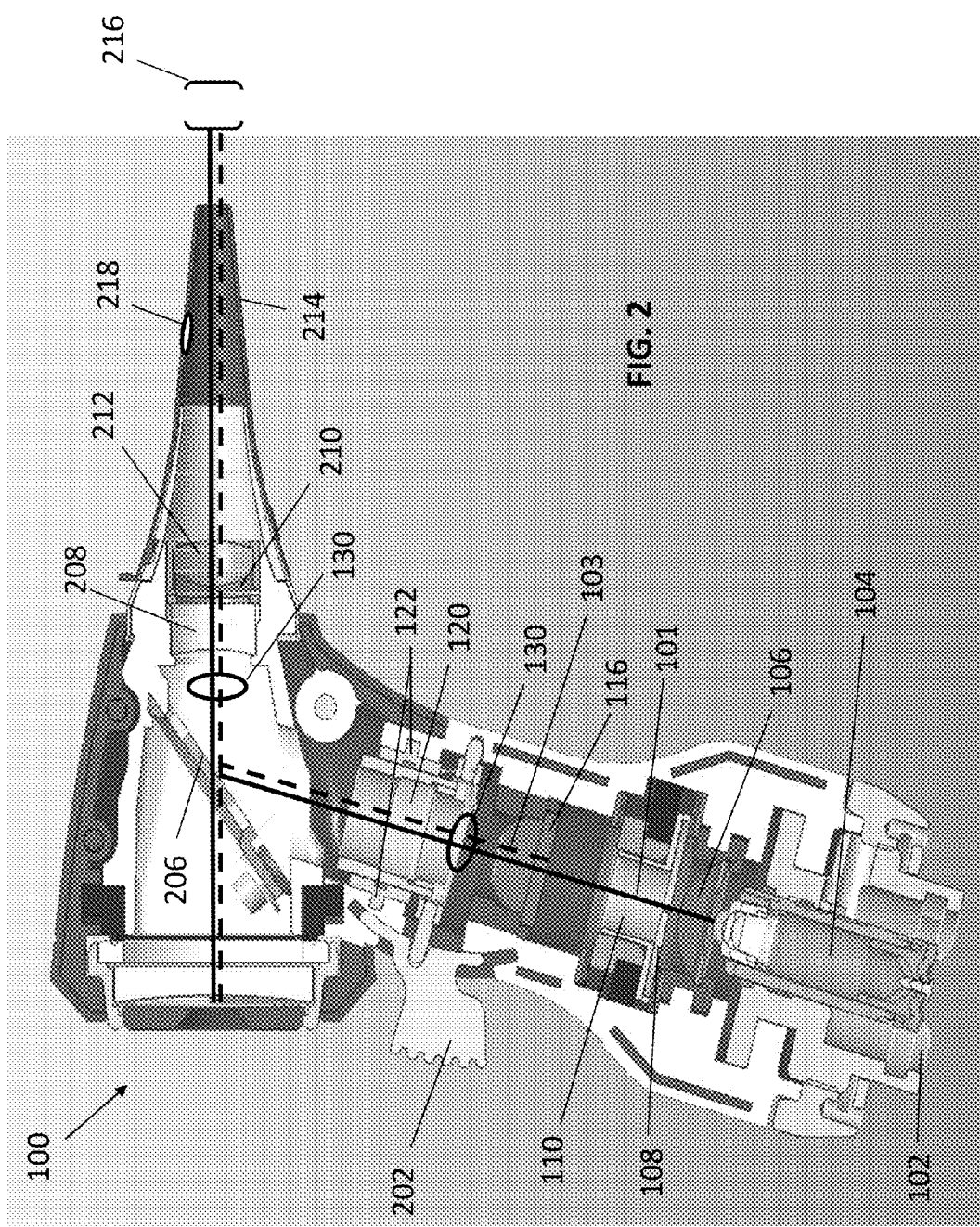

FIGS. 1-2 depict illustrative embodiments of rear and side cross-sectional views of a probe 100. From the rear view shown in FIG. 1, the probe 100 comprise a mechanical sub-assembly 102 that can couple to a tethered power source or a battery accessory which can be engaged with the probe 100 by a rotational or axial mechanism (not shown). The tethered power source or battery accessory can be used to supply a power signal to a superluminescent diode 104 (herein referred as diode 104), which serves as a first light source in the probe 100. The diode 104 operates in a first region of the light spectrum (e.g., 5-100 nanometers-nm). The diode 104 enables visualization of a target such as biological or non-biological material. It will be appreciated that the diode 104 can be replaced with other light sources such as a halogen-based light source, an electroluminescent light source, a phosphor-luminescent light source, a filament light source, a light emitting polymer light source, or a laser light source. These and other suitable light sources are contemplated by the present disclosure.

A first light signal 101 emitted by the diode 104 can be focused with a condensing lens 106. The focused light passes through a marking device 108 for projecting a mark on the target (e.g., cross-hairs). The focused light continues through a cavity 110 and traverses an optical component 116. The optical component 116 can be, for example, a mirror, which allows the first light signal 101 emitted by the diode 104 to traverse a bottom surface of the optical component 116 and exit a top surface of the optical component 116 substantially without diffraction, while the optical component 116 orthogonally reflects at its top surface a second light signal 103 emitted by a fiber 118 coupled to a second light source (see reference 502 in FIG. 5). The second light signal 103 operates in a near-infrared portion of the light spectrum.

In more detail, the optical component 116 can be a hot mirror having the properties of reflecting from a top surface light signals operating in the near-infrared portion of the light spectrum and allowing light signals operating in another portion of the light spectrum (e.g., 5-100 nm) to traverse the mirror from a bottom surface and exiting the top surface without diffraction. The optical component 116 can be positioned between the diode 104 and the fiber 118 so that the focal points of the first and second light signals 101 and 103, respectively, are coincident (or nearly coincident) with each other as will be described later in reference to FIGS. 3-4.

Once the second light signal 103 is orthogonally reflected by the optical component 116, the first light signal 101 and the second light signal 103 converge on a coaxial optical path 130, which continues through a focusing lens 120. The focusing lens 120 can be coupled to a slideable subassembly 122, which enables adjustment of a position of the focusing lens 120 so that the focal points of both the first and second light signals 101 and 103 can be moved simultaneously to a new position without changing the relative distance between the focal points of the first and second light signals 101 and 103. The thumbwheel 202 shown in FIG. 2 illustrates a way to mechanically adjust the slideable assembly 122. It will be appreciated that the thumbwheel can be replaced with a slideable mechanical pin, or other manual or motorized mechanism.

After traversing the focusing lens 120, a portion of the coaxial optical path 130 of the first and second light signals 101 and 103 is orthogonally reflected off a surface of a beam splitter 206 and is redirected to a first lens 208, a second lens 210, and a third lens 212 before reaching a speculum 214 (which can be modular, i.e., replaceable to accommodate different targets). The first, second, and third lens 208, 210 and 212 help to correct aberrations in the light signals and provide a means to magnify a viewing of the mark on a target 216 by way of an observation window 124 shown in FIG. 1.

Upon reflecting from the target 216, the first and second light signals 101, 103 travel on a reverse coaxial optical path 130 traversing the first, second and third lenses 208, 210, 212 in reverse order towards the beam splitter 206, which allows a first portion (e.g., 50% of the first and second light signals 101, 103) to travel through the beam splitter 206 without reflection towards the observation window 124 shown in FIG. 1. The observation window 124 enables a visualization of the mark (e.g., cross-hairs) associated with the first light signal 103 that reflects from the target 216. Since near-infrared light is not visible, it is not possible to see the reflection of the second light signal 103 from the target 216.

A second portion (e.g., 50%) of the first and second light signals 101, 103 of the reverse coaxial optical path 130 reflect from the beam splitter 206 and travel towards the optical component 116 after traversing the focusing lens 120. The second light signal 103 reflects from the optical component 116 and travels towards the fiber 118 and continues on a path for processing by a system 500 shown in FIG. 5.

Figure 3:
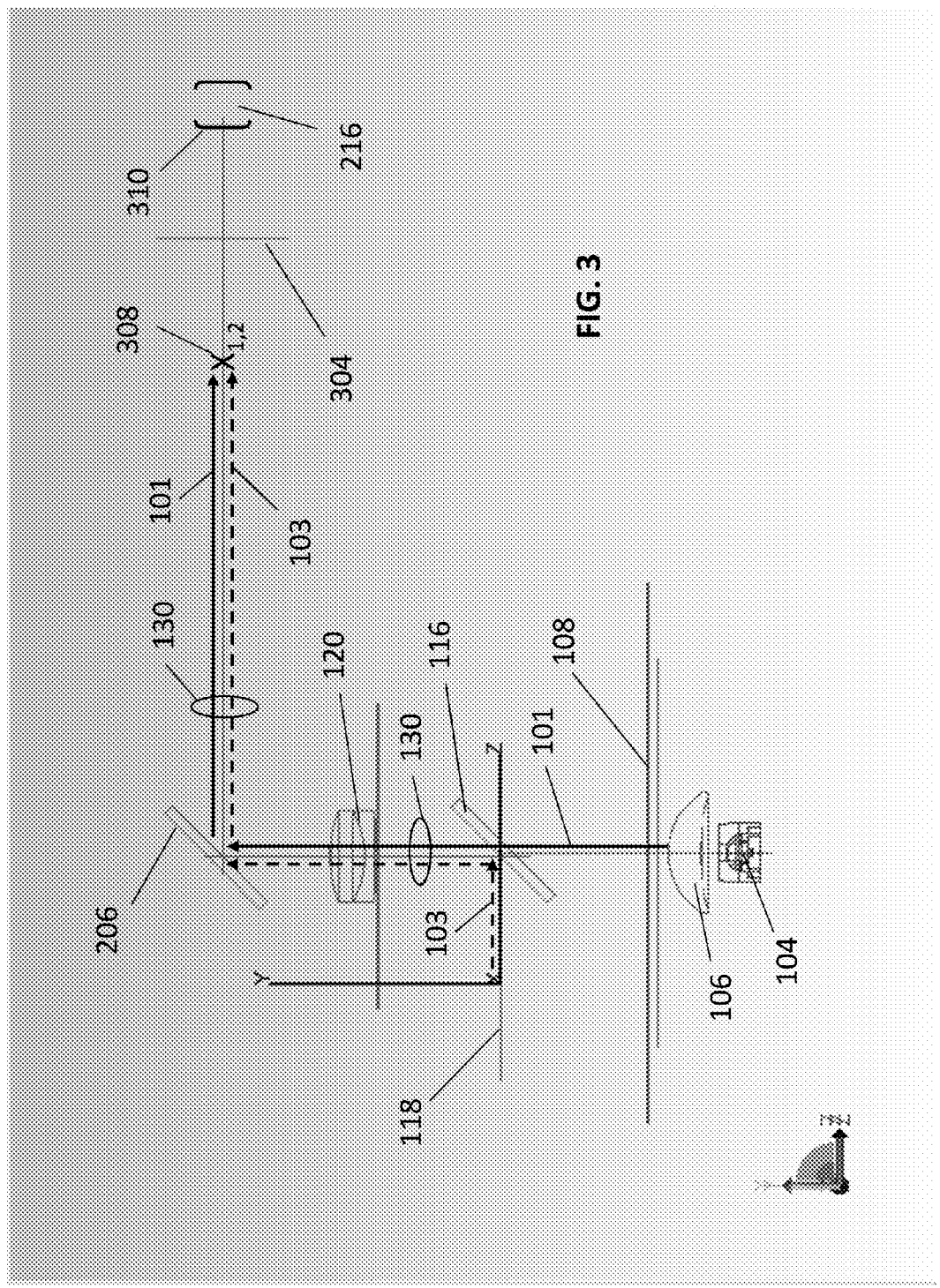
FIGS. 3-4 depict illustrative embodiments of optics configurations of the probe of FIGS. 1-2.
Figure 4:
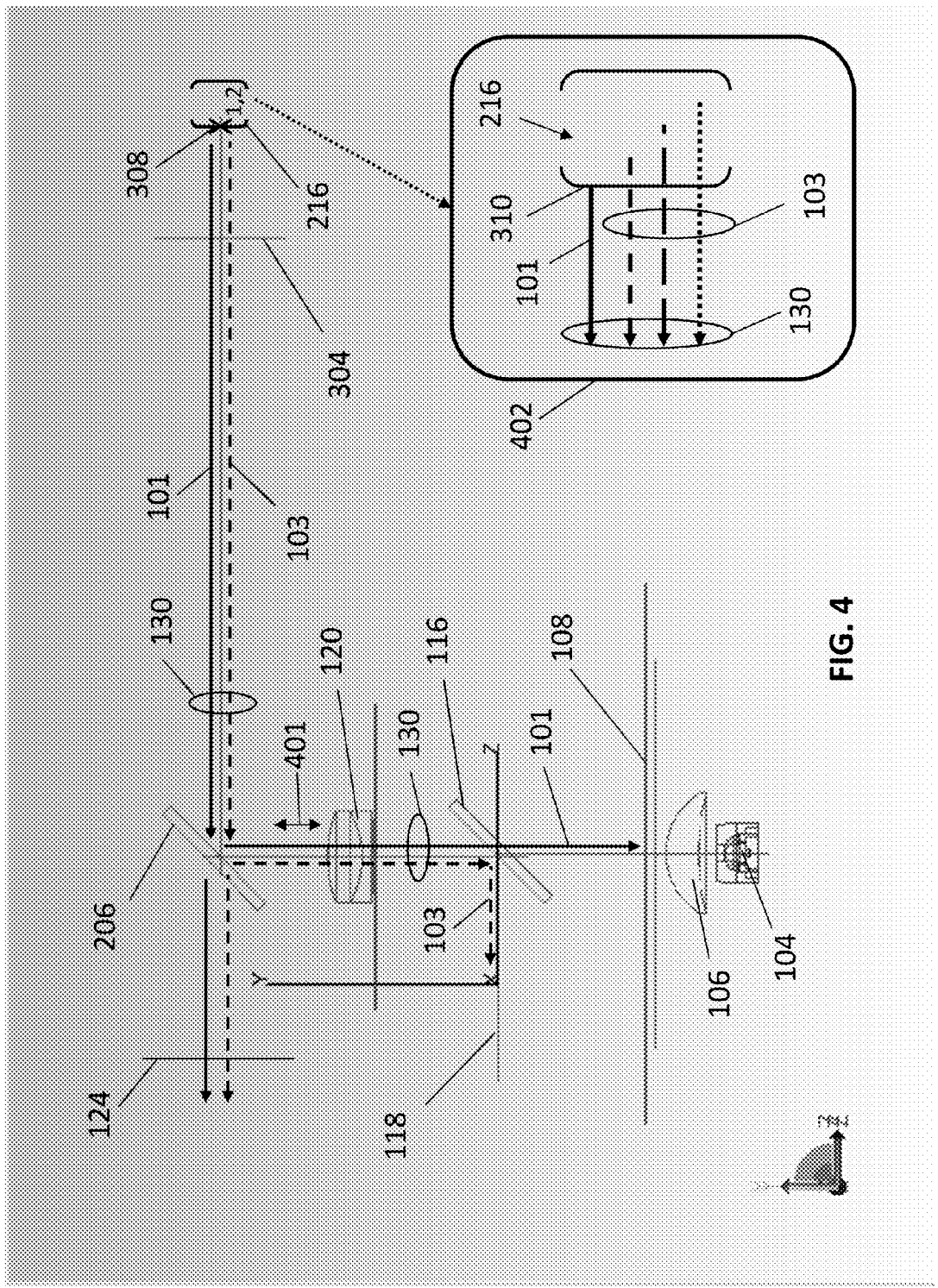

FIGS. 3-4 illustrate an embodiment for positioning the optical component 116 between the diode 104 and the fiber 118 in order to align the focal points of each light source so that they coincide at location 308 (depicted by the symbol "$X_{1,2}$", representing focal point 1 of the first light signal 101 and focal point 2 of the second light signal 103). In particular, FIG. 3 illustrates the input paths of each light source towards a target 216, while FIG. 4 illustrates the return paths of each light source from target 216. In one embodiment, the optical component 116 can be positioned within the probe 100 so that it is located a first distance measured from a starting point of the first light signal 101 emitted by the condensing lens 106 to a point of contact of the first light signal 101 on a bottom surface of the optical component 116, and a second distance measured from a starting point of the second light signal 103 emitted by the fiber 118 to a point of contact of the second light signal 103 on a top surface of the optical component 116. Using known optical design principles, with an understanding of the properties of the optical component 116 (such as the optical component's thickness, composition, and so on), one can choose the first and second distances such that the focal points of the first and second light signals 101 and 103 are coincident (or nearly coincident) with each other at location 308.

In the illustration of FIG. 3, location 308 is shown before the egress point of the speculum 214 depicted by reference 304. To perform measurements of the subsurfaces of the target 216, the focal points of the first and second light signals 101 and 103 should be repositioned at approximately a top surface of the target 216. This can be accomplished by adjusting the focusing lens 120 using the thumbwheel 202 shown in FIG. 2. By adjusting the thumbwheel 202 and visualizing through window 124 the mark produced by the first light signal 101, a user of the probe 100 can reposition the focal points on the target 216 as illustrated in FIG. 4. In this illustration, the focusing lens 120 is moved (depicted by the up/down arrow 401) so that the focal points ($X_{1,2}$) are placed at approximately a top surface of the target 216 without separating the focal points from each other. An expanded view of the target 216 is depicted with reference 402 to illustrate what happens once the focal points have been repositioned on the target 216.

In this illustration, the first light signal 101 is reflected from the top surface 310 of the target 216 with minimal penetration of the target. This is because the first light signal 101 can be chosen to operate in a first portion of the light spectrum such that the first light signal 101 reflects with minimal or no penetration of the target 216. The second light signal 103, however, is chosen to operate in a second portion of the light spectrum to enable so that it penetrates a portion of subsurfaces of the target 216 thereby causing a scattering of reflections at varying depths (shown by the multitude of light rays emanating from the target 216).

The reflections as noted earlier travel on a reverse coaxial optical path 130. A portion of the first light signal 101 travels through the beam splitter 206, thereby providing the user of the probe 100 a means to visualize the position of the mark (e.g., cross-hairs) on the top surface 310 of the target 216. Once the user focuses the cross-hairs on the top surface 310 of the target 216, the focal point of the second light signal 103 is also focused on the top surface 310 since the distance between the focal points of both light signals remains unchanged. The mark associated with the first light signal 101 serves as an aid for placing the focal point of the second light signal 103 on the top surface 310 of the target 216 since the user of the probe 100 is unable to see near-infrared light. As described earlier, the scattered reflections of the second light signal 103 travel back through the optical system of the probe 100 to the fiber 118 on a path for processing by system 500 in FIG. 5.

System 500 can comprise a broadband source 502, which generates near-infrared light which is split by a beam splitter 504 into two light signals, sending a reference signal to a reference mirror 506 and a sample signal to the probe 100 via the fiber 118. The reflected reference signal from the reference mirror 506 and the scattered reflections of the second light signal 103 travel through the beam splitter 504 to a computing device 508 capable of sensing an interference pattern of near-infrared light reflected from the target 216 and the reference signal reflected from the reference mirror 506.

Figure 9:
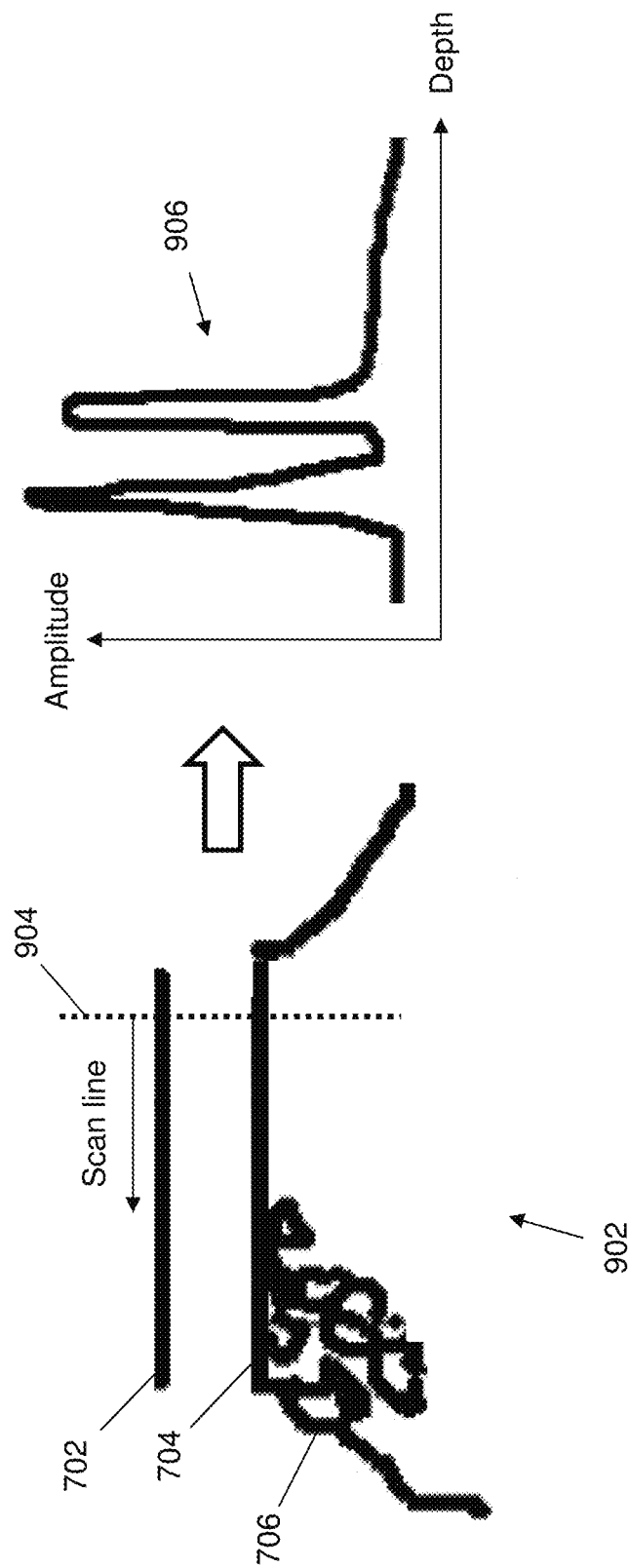

The computing device 508 can utilize, for example, an optical coherence tomography (OCT) spectrometer to analyze the interference and provide signal plots and/or imaging information which can be displayed on a presentation device 510. Samples of signal plots and an OCT image generated by an OCT spectrometer are shown in FIGS. 7-9. Images generated by the OCT spectrometer can be two or three dimensional images descriptive of the subsurfaces of the target 216 and can be displayed contemporaneously with a signal plot such as shown in FIG. 9.

System 500 can be used in various applications where analyzing subsurfaces of target materials is desirable. For example, system 500 can be utilized in medical applications such as in the case of an OCT otoscope probe having the optical system described above for probe 100 (referred to herein as OCT probe 100). A physician or nurse practitioner can, for example, place the speculum 216 of the OCT probe 100 in an ear cavity of a patient, and with thumbwheel 202 focus the cross-hairs on the patient's tympanic membrane, which can be visualized through the observation window 124.

Once the cross-hairs have been focused, the clinician can visualize on display 510 signal plots and/or OCT images descriptive of the subsurfaces of the tympanic membrane. If the patient's tympanic membrane is healthy, the physician or nurse can expect to see a signal plot that is indicative of a normal membrane such as shown in FIG. 7. If the tympanic membrane has an abnormal structure such as a biofilm behind the eardrum, which is indicative of otitis media, a common illness in children, the clinician can expect to see a signal plot such as shown in FIG. 8. The OCT probe 100 can be designed with removable speculums to enable the physician or nurse to select a speculum that best fits the patient. Also the speculums can be designed with an opening 218 enabling an insertion of, for example, a curette to remove cerumen (earwax) or a foreign object.

Figure 5:
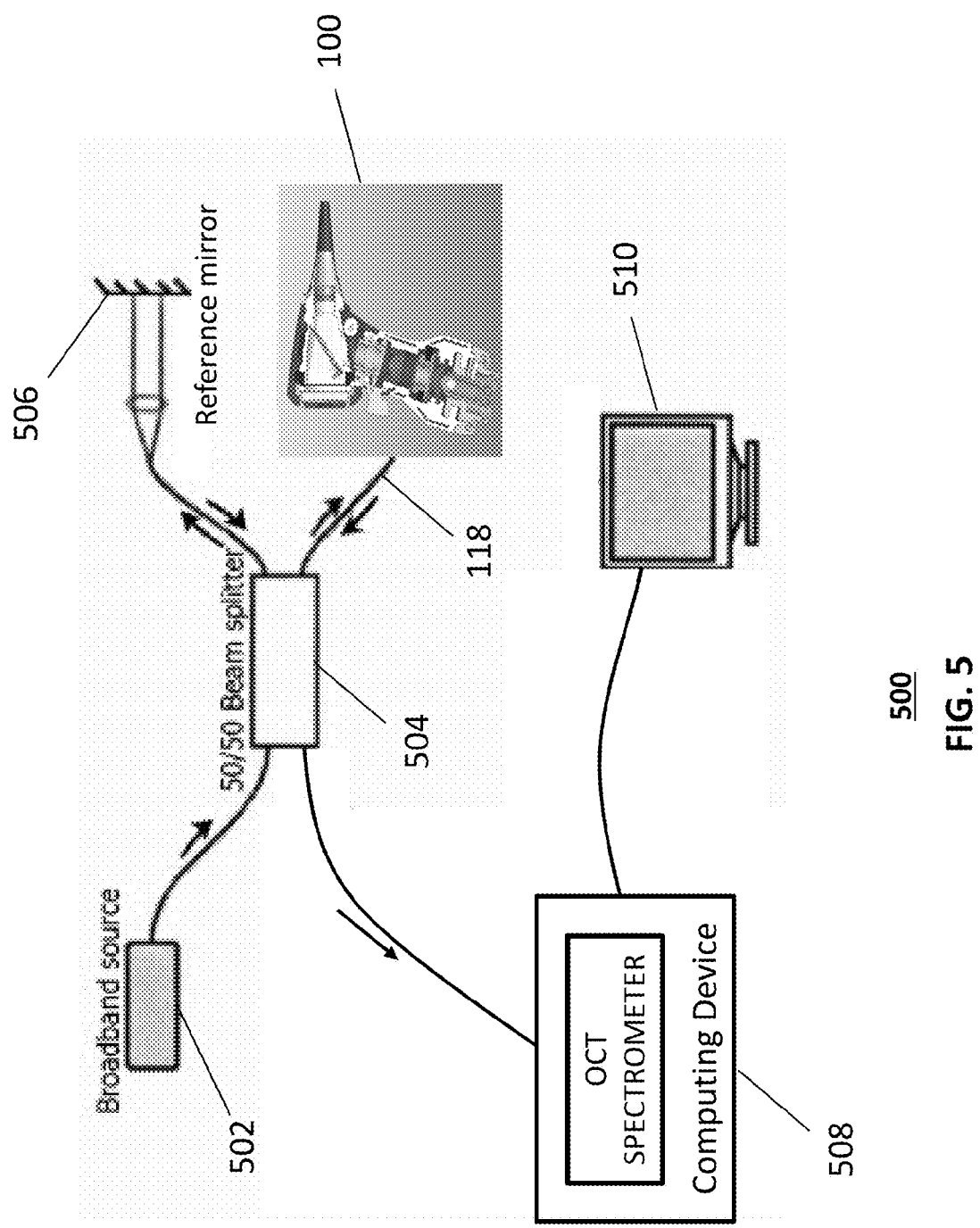
FIG. 5 depicts an illustrative embodiment of an imaging system utilizing the probe of FIGS. 1-2.
Figure 6:
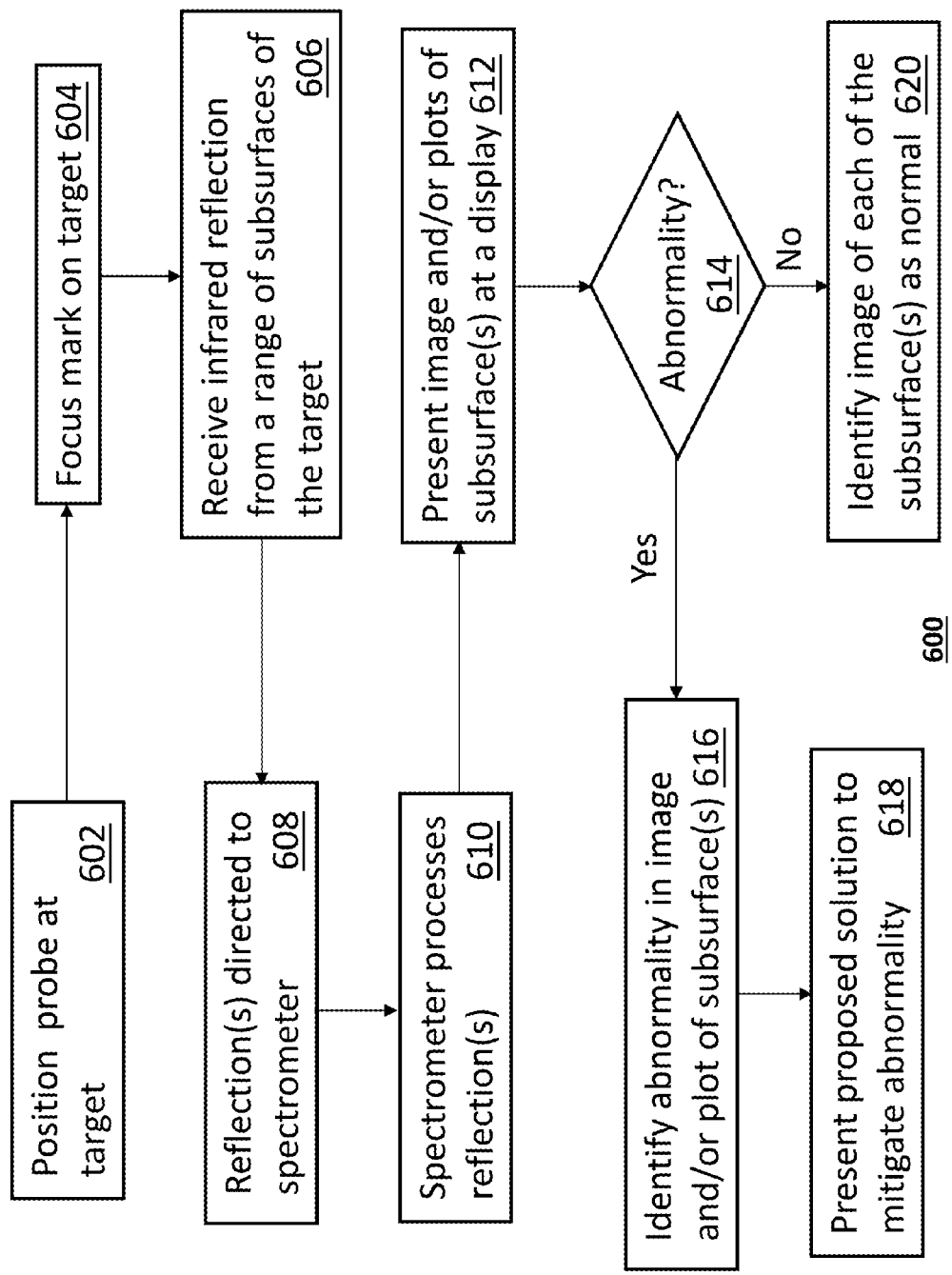
FIG. 6 depicts an illustrative embodiment of a method operating in portions of the system of FIG. 5.

FIG. 6 depicts an illustrative method 600 that can operate in portions of the devices of system 500 of FIG. 5. Method 600 can be implemented with executable software, hardware, or combinations thereof in portions of the components shown in system 500. Method 600 can begin with step 602 in which probe 100 is positioned at the target 216. At step 604, a user of the probe 100 focuses a cross-hair mark (or other noticeable mark) on the target 216. The probe 100 receives near infrared reflections from a range of subsurfaces of the target 216 at step 606, which are directed to the spectrometer 508 at step 608. The spectrometer 508 processes the interference in reflections relative to a reference signal at step 610, and presents at step 612 images and/or plots such as shown in FIGS. 7-9 descriptive of the subsurfaces at the display 510.

Method 600 can be further adapted to determine at step 614 whether an abnormality exists. This step can be accomplished by statistical modeling of normal versus abnormal targets, or by recording signal profiles and/or image profiles of normal and abnormal targets, which can be retrieved from a database stored in the computing device 508 of FIG. 5 or at a remote database (not shown). For example, the signal profile of the reflected near-infrared signals can be used to detect the presence of an abnormality, while the reflected light from the first signal 101 can be used to identify the type of abnormality by measuring a range of wavelengths (color) of the reflected first signal 101 and/or its fluorescence. The reflected first signal 101 can be detected by a camera sensor integrated in the probe 100, such as a charge-coupled device (CCD) sensor, to project images on a display such as display 510 of system 500. A spectrometer signal can also be projected on display 510.

A clinician can then visualize the color and/or fluorescence of the images of the target 216 along with spectrometer signal plots to assess a type of abnormality that may be known to the clinician from prior experiences. Alternatively, image and signal processing software can be utilized by the computing device 508 to determine from the signal profile of the reflected near-infrared light and the wavelength and/or fluorescence of the reflected first signal 101 to automatically determine a presence and type of abnormality by comparing the detected light signals to normal and abnormal profiles stored in a local or remote database. Such profiles can be collected in clinical trials using statistical modeling and/or other techniques suitable for profiling targets.

If no abnormalities are detected, the computing device 508 proceeds to step 620 where it presents the image and/or plots of the subsurfaces of a normal target. If an abnormality is found in the target 216, the computing device 508 can proceed to step 616 where it can identify the abnormality in the image or plot of the subsurfaces of the target 216. The computing device 508 can be further adapted in step 618 to analyze the abnormality and propose a solution to mitigate the abnormality. In a medical setting, the proposed solution could be, for example, a proposed prescription of medicine or method of treatment for the patient. In an industrial setting, the proposed solution could be an identification of an area of the target 216 having fractures that should be avoided.

FIGS. 7-8 depict how the reflected light signals supplied by the probe 100 for processing by a spectrometer can produce signal plots that can be used for analyzing target subsurfaces. FIG. 7 depicts a cross-section of a physical target. In the illustration the target has a top surface 702 and a bottom surface 704. When the near-infrared signal travels through optical path A with no obstruction (i.e., no foreign matter at the bottom surface 704), it reflects from both the top and bottom surfaces 702 and 704 with minimal scattering. The spectrometer 508 can then process the reflected signals and produce the signal plots shown in FIG. 8A. FIG. 8A shows a first signal spike 802 representative of the top surface 702 and a second signal spike 804 representative of the bottom surface 704. Since there are no obstructions, the magnitude of the signals are strong.

When the near-infrared signal travels through optical path B and an obstruction is present such as foreign matter 706 at the bottom surface 704, the near-infrared signal reflects from both the top surface 702 with minimal scattering, while it reflects from the bottom surface 704 with a substantial amount of scattering, which dampens the signal reflection. The spectrometer 508 can then process the reflected signals and produce a first signal spike 806 representative of the top surface 702 and a second signal spike 808 representative of the bottom surface 704 as shown in FIG. 8B. The dampening of the second signal spike 808 is indicative that foreign matter (e.g., a biofilm in the case of biological tissue) is present behind the bottom surface 704.

The wavelengths of the first light signal 101 reflected from the target 216 can be detected with a CCD sensor for producing color images which may enable a user of the probe 100 to identify a type of foreign matter (e.g., type of biofilm). Alternatively, the computing device 508 can be adapted to automatically analyze the target 216 using image and signal processing techniques to diagnose and prescribe to a user of the probe 100 a solution that mitigates foreign matter detected at a subsurface of the target 216. It is further noted that probe 100 can be adapted to cause the first and second light sources to repeatedly sweep the first and second light signals 101 and 103 across a surface area of the target 216 to enable the computing device 508 to gather sufficient data to provide the clinician a two or three dimensional analysis of the target 216.

This can be accomplished by coupling one of the optical components in the coaxial optical path 130 to a mechanism that causes the optical component to vibrate in such a way as to cause the first and second light signals 101 and 103 to sweep a surface area of the target 216. The reflected light signals provide the computing component 508 sufficient information to provide a clinician the ability to readily analyze different portions of the target 216. FIG. 9 illustrates a cross-sectional image plot 902 of the target 216 and its subsurfaces, and a signal plot 906 representative of reflections from subsurfaces at a position of the scan line 904. Computing device 508 can be adapted to provide a clinician the ability to move the scan line 904 left and right with a navigation device (e.g., left and right arrows on a keyboard). As the scan line 904 moves, the signal plot 906 changes according to the scanned data collected by the spectrometer.

Upon reviewing the aforementioned embodiments, it would be evident to an artisan with ordinary skill in the art that said embodiments can be modified, reduced, or enhanced without departing from the scope and spirit of the claims described below. For example, the otoscope described in U.S. Pat. No. 3,698,387, filed Oct. 7, 1969, entitled "Otoscope Construction," and/or in U.S. Pat. No. 7,399,275, filed Jul. 23, 2004, entitled "Otoscope" can be adapted according to the features described above for probe 100. All sections of the aforementioned patents are incorporated herein by reference in their entirety. In another embodiment, the probe 100 can be adapted for endoscopy. The optical system of probe 100 can be integrated in an endoscope for performing multiple forms of endoscopic analysis (e.g., esophagogastroduodenoscopy, enteroscopy, colonoscopy, rhinoscopy, cystoscopy, hysteroscopy, and so on). For example, the optical system of probe 100 can be placed near a tip of an endoscope to analyze abnormalities such as ulcerations or polyps discovered during a colonoscopy without performing a biopsy.

Probe 100 can also be adapted to analyze skin tissue for melanoma or other cancerous conditions. Probe 100 can also be adapted for industrial applications in which the optical system of the probe 100 is inserted in a drill bit for purposes of analyzing a target prior to or during a drilling action. Probe 100 can be further adapted to perform an autofocus function in order to remove the thumbwheel 202 of FIG. 2. In this embodiment, linear or stepper motors can be added to the probe 100 to move the focus lens 120. Auto-focusing techniques such as passive auto focusing can be used to determine the location of the target 216. For example, phase detection can be used for auto focusing the first light signal 101 on the target 216 by dividing incoming light into pairs of images and comparing them. The phase difference between the images can be measured using image processing means. The detected phase difference can be used to direct an adjustment of the focusing lens 120 by way signals sent to the linear or step motors. The computing device 508 can be adapted to process these measurements and control the focusing process, or a miniature computing device can be integrated in the probe 100 to perform this function. Other embodiments are contemplated by the subject disclosure.

Figure 10:
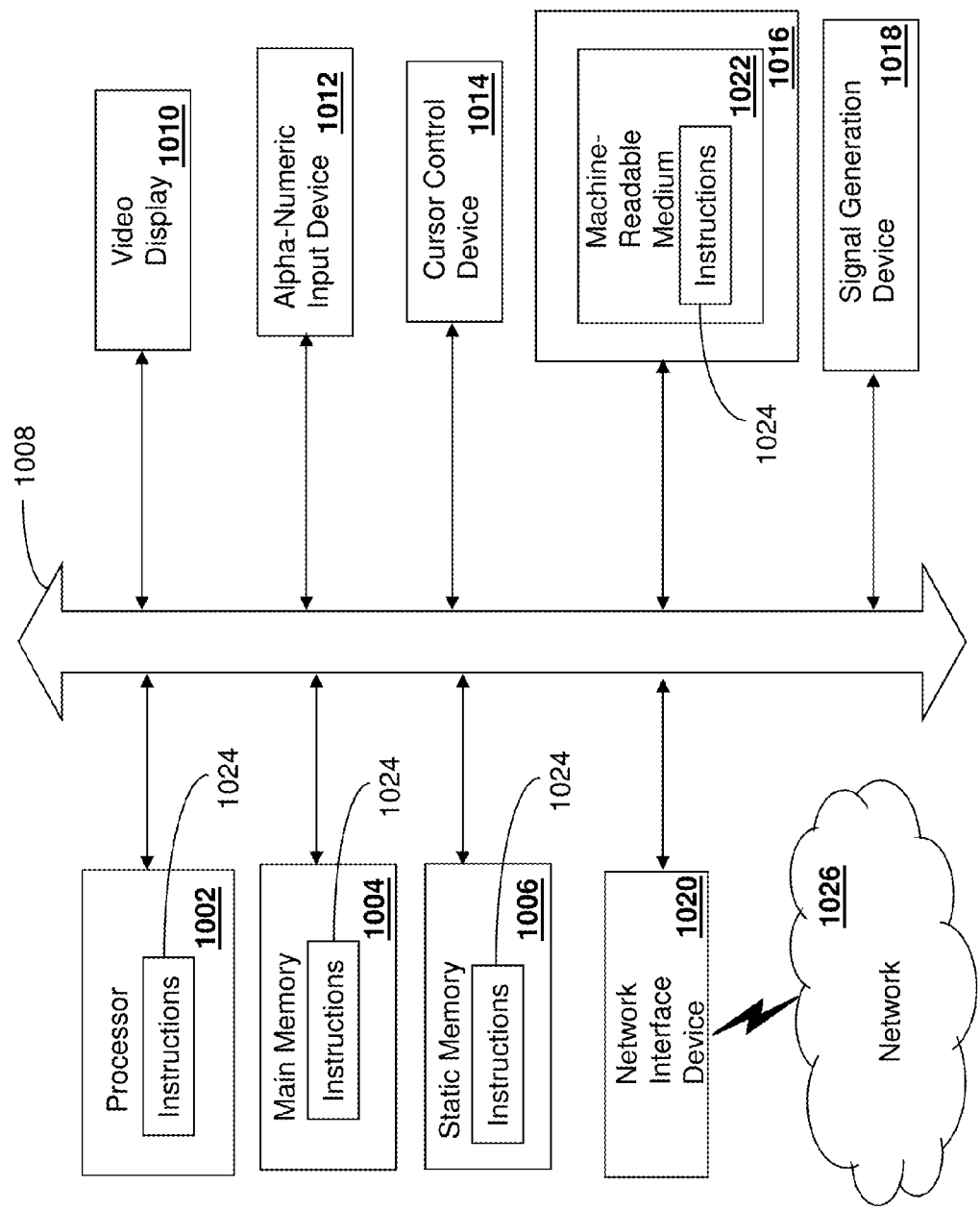
FIG. 10 is a diagrammatic representation of a machine in the form of a computer system within which a set of instructions, when executed, may cause the machine to perform any one or more of the methods described herein.

FIG. 10 depicts an exemplary diagrammatic representation of a machine in the form of a computer system 1000 within which a set of instructions, when executed, may cause the machine to perform any one or more of the methods discussed above. One or more instances of the machine can operate, for example, as the components shown in FIG. 5. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 1000 may include a processor 1002 (e.g., a central processing unit (CPU), a graphics processing unit (GPU, or both), a main memory 1004 and a static memory 1006, which communicate with each other via a bus 1008. The computer system 1000 may further include a video display unit 1010 (e.g., a liquid crystal display (LCD), a flat panel, or a solid state display. The computer system 1000 may include an input device 1012 (e.g., a keyboard), a cursor control device 1014 (e.g., a mouse), a disk drive unit 1016, a signal generation device 1018 (e.g., a speaker or remote control) and a network interface device 1020.

The disk drive unit 1016 may include a tangible computer-readable storage medium 1022 on which is stored one or more sets of instructions (e.g., software 1024) embodying any one or more of the methods or functions described herein, including those methods illustrated above. The instructions 1024 may also reside, completely or at least partially, within the main memory 1004, the static memory 1006, and/or within the processor 1002 during execution thereof by the computer system 1000. The main memory 1004 and the processor 1002 also may constitute tangible computer-readable storage media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

While the tangible computer-readable storage medium 1022 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID), short-range communications (e.g., Bluetooth, WiFi, Zigbee), and long-range communications (e.g., WiMAX, GSM, CDMA, LTE) are contemplated for use by computer system 1000.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, are contemplated by the subject disclosure.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A device, comprising:
   a first light source for emitting a first light signal;
   a second light source for emitting a second light signal, wherein the first light signal and the second light signal differ; and
   an optical component that coaxially aligns the first light signal and the second light signal, wherein the optical component maintains a first focal point of the first light signal in at least a proximate location of a second focal point of the second light signal, and wherein the optical component further maintains the first focal point at the proximate location of the second focal point after a focal adjustment of the first focal point or the second focal point.

2. The device of claim 1, wherein the first light signal operates in a first region of a light spectrum, and wherein the second light signal operates in a second region of the light spectrum.

3. The device of claim 2, wherein the first region and the second region differ.

4. The device of claim 1, wherein the first light signal enables visualization of a target.

5. The device of claim 1, wherein the second light signal reflects a portion of the second light signal from a subsurface of a target.

6. The device of claim 5, wherein the target comprises a tissue.

7. The device of claim 5, wherein the portion of the second light signal reflected from the subsurface of the target when processed by a computing device identifies an aberration of the target.

8. The device of claim 5, wherein the portion of the second light signal reflected from the subsurface of the target is directed to a system that detects a signal from the subsurface of the target.

9. The device of claim 8, wherein the system comprises a spectrometer that processes the signal.

10. The device of claim 1, comprising a beam splitter incident with a coaxial path of the first light signal and the second light signal.

11. The device of claim 1, wherein the first light source comprises a light emitting diode.

12. The device of claim 1, wherein the second light source comprises a laser.

13. A method, comprising:
- receiving from a device a portion of a first light signal reflected from a subsurface of a target, wherein the device coaxially aligns the first light signal and a second light signal and maintains a first focal point of the first light signal in at least a proximate location of a second focal point of the second light signal;
- directing the device to perform a focal point adjustment of the first focal point or the second focal point, wherein the device maintains the first focal point at the proximate location of the second focal point after the focal point adjustment;
- receiving from the device an updated instance of the first light signal reflected from the subsurface of the target responsive to the focal point adjustment; and
- producing from the updated instance of the first light signal an output for analyzing the subsurface.

14. The method of claim 13, further comprising determining from the output a presence of an aberration in the target.

15. The method of claim 13, wherein the first light signal is produced by a first light source comprising a light emitting diode.

16. The method of claim 13, wherein the second light signal is produced by a second light source comprising comprises a laser.

17. The method of claim 13, wherein the target comprises a biological tissue.

18. A non-transitory machine-readable storage device, comprising instructions, which when executed by a processor, cause the processor to perform operations comprising:
- receiving a first light signal reflected from a subsurface of a target, wherein an optical component coaxially aligns the first light signal with a second light signal, and wherein a relative position of the optical component to a first light source of the first light signal and a second light source of the second light signal provides a first focal point of the first light signal to be in a proximate location of a second focal point of the second light signal;
- performing a focal point adjustment of the first focal point or the second focal point, wherein the relative position of the optical component maintains the first focal point at the proximate location of the second focal point after the focal point adjustment;
- receiving from the optical component an updated instance of the first light signal reflected from the subsurface of the target responsive to the focal point adjustment; and
- producing from the updated instance of the first light signal an image relating to the subsurface.

19. The non-transitory machine-readable storage device of claim 18, wherein the first light signal operates in a first region of a light spectrum for reflecting portions of the first light signal from the subsurface of the target.

20. The non-transitory machine-readable storage device of claim 18, wherein the second light signal operates in a second region of a light spectrum enabling visualization of the target.

* * * * *